United States Patent
Morimoto

(10) Patent No.: US 9,863,067 B2
(45) Date of Patent: Jan. 9, 2018

(54) CRIMPED CONJUGATED FIBER AND NON-WOVEN FABRIC COMPRISING THE FIBER

(75) Inventor: Hisashi Morimoto, Ichihara (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 563 days.

(21) Appl. No.: 13/637,382

(22) PCT Filed: Apr. 4, 2011

(86) PCT No.: PCT/JP2011/058503
§ 371 (c)(1),
(2), (4) Date: Sep. 26, 2012

(87) PCT Pub. No.: WO2011/129211
PCT Pub. Date: Oct. 20, 2011

(65) Prior Publication Data
US 2013/0029555 A1    Jan. 31, 2013

(30) Foreign Application Priority Data
Apr. 16, 2010 (JP) .................. 2010-095368

(51) Int. Cl.
*D01F 8/06* (2006.01)
*A61F 13/511* (2006.01)
(Continued)

(52) U.S. Cl.
CPC ............. *D01F 8/06* (2013.01); *A61F 13/511* (2013.01); *A61F 13/512* (2013.01); *D01D 5/22* (2013.01);
(Continued)

(58) Field of Classification Search
CPC ............. D02G 3/02; D04H 3/005; D01F 8/06
(Continued)

(56) References Cited

U.S. PATENT DOCUMENTS 3,900,678 A * 8/1975 Aishima et al. .............. 428/374
5,108,820 A * 4/1992 Kaneko et al. .............. 428/198
(Continued)

FOREIGN PATENT DOCUMENTS

JP   2-191720 A   7/1990
JP   7-197367 A   8/1995
(Continued)

OTHER PUBLICATIONS

Extended European Search Report dated Nov. 29, 2013, by the European Patent Office in corresponding European Patent Application No. 11768732.7. (6 pages).

*Primary Examiner* — Andrew Piziali
(74) *Attorney, Agent, or Firm* — Buchanan, Ingersoll & Rooney PC

(57) ABSTRACT

The present invention provides a crimped conjugated fiber having a crimpable cross-sectional configuration wherein a cross section of the fiber comprises at least two portions: a portion (a) and a portion (b); the portion (a) comprises a propylene polymer (A) and the portion (b) comprises a propylene/α-olefin random copolymer (B); the propylene polymer (A) has Mz/Mw(A) and the propylene/α-olefin random copolymer (B) has Mz/Mw(B) wherein the difference thereof is in the range of 0.10 to 2.2; and the propylene polymer (A) has a melting point [Tm(A)] and the propylene/α-olefin random copolymer (B) has a melting point [Tm(B)] wherein the difference thereof exceeds 10° C. The present invention also provides a non-woven fabric comprising the crimped conjugated fiber.

6 Claims, 2 Drawing Sheets

(51) Int. Cl.

| | | |
|---|---|---|
| *A61F 13/512* | (2006.01) | |
| *D04H 1/4291* | (2012.01) | |
| *D04H 1/541* | (2012.01) | |
| *D04H 3/018* | (2012.01) | |
| *D04H 3/147* | (2012.01) | |
| *D04H 3/16* | (2006.01) | |
| *D01D 5/22* | (2006.01) | |
| *D04H 3/007* | (2012.01) | |

(52) U.S. Cl.
CPC ........... *D04H 1/4291* (2013.01); *D04H 1/541* (2013.01); *D04H 3/007* (2013.01); *D04H 3/018* (2013.01); *D04H 3/147* (2013.01); *D04H 3/16* (2013.01); *Y10T 428/2924* (2015.01); *Y10T 442/641* (2015.04)

(58) Field of Classification Search
USPC ........ 442/361, 364, 409, 414, 415; 428/364, 428/365, 369, 370, 371, 373, 374
See application file for complete search history.

(56) References Cited

U.S. PATENT DOCUMENTS

| | | | | |
|---|---|---|---|---|
| 5,462,807 | A | * | 10/1995 | Halle et al. .................... 428/500 |
| 6,143,854 | A | * | 11/2000 | Bamberger et al. ........ 526/348.1 |
| 6,306,973 | B1 | * | 10/2001 | Takaoka et al. ............... 525/240 |
| 6,451,915 | B1 | * | 9/2002 | Ellul et al. ..................... 525/191 |
| 6,454,989 | B1 | | 9/2002 | Neely et al. |
| 6,500,538 | B1 | | 12/2002 | Strack et al. |
| 2004/0067709 | A1 | | 4/2004 | Kishine et al. |
| 2007/0021022 | A1 | | 1/2007 | Kishine et al. |
| 2007/0275622 | A1 | | 11/2007 | Masuda et al. |
| 2008/0071032 | A1 | * | 3/2008 | Massari et al. ................ 525/240 |
| 2011/0189915 | A1 | | 8/2011 | Morimoto et al. |

FOREIGN PATENT DOCUMENTS

| | | |
|---|---|---|
| JP | 2002-180331 A | 6/2002 |
| JP | 2007-308868 A | 11/2007 |
| WO | 2007/097467 A1 | 8/2007 |
| WO | WO 2010/050407 A1 | 5/2010 |

* cited by examiner

[Fig. 1]
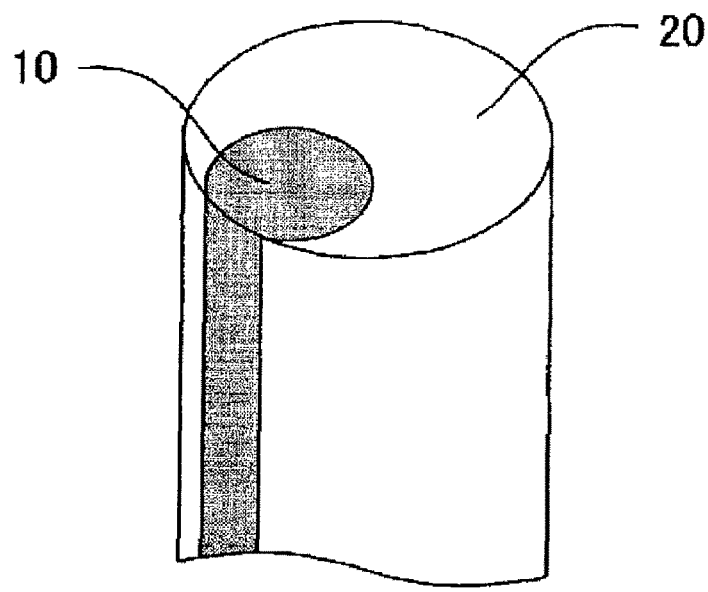
[Fig. 2]
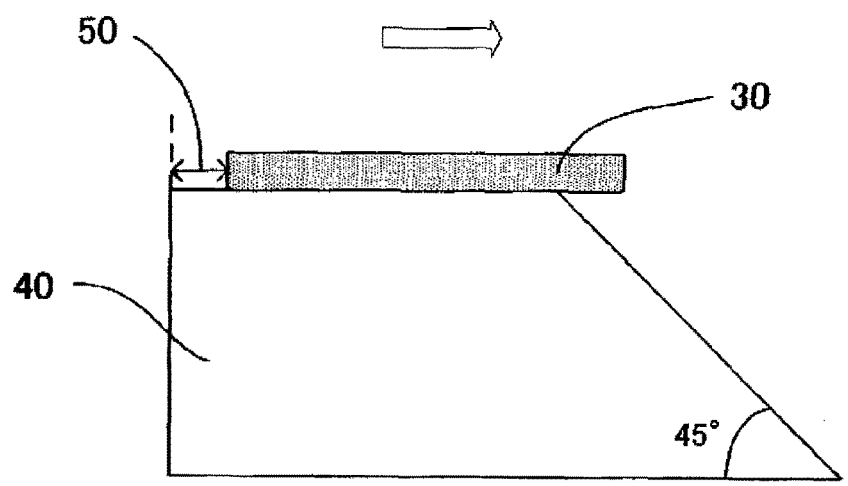
[Fig. 3]
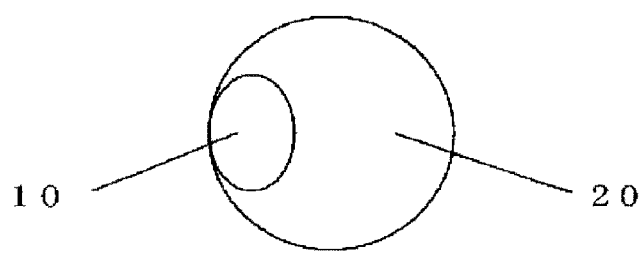

[Fig. 4]
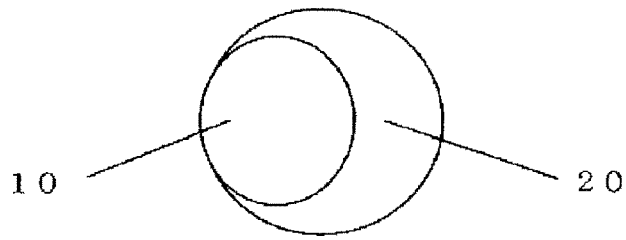
[Fig. 5]
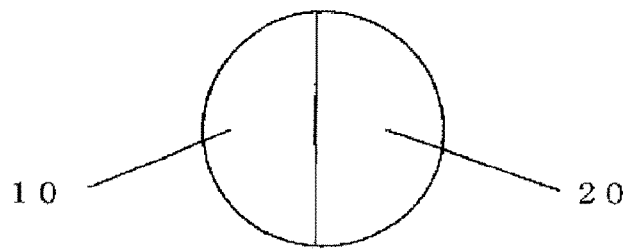
[Fig. 6]
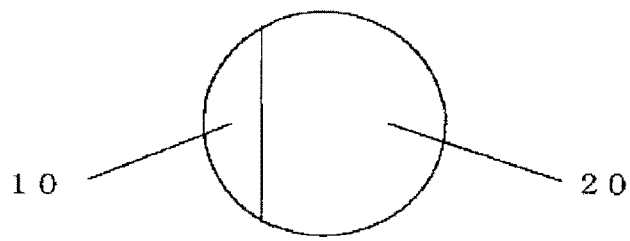
[Fig. 7]
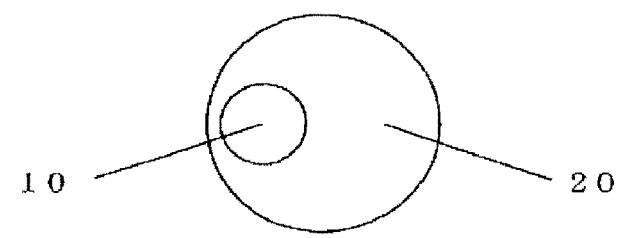
[Fig. 8]
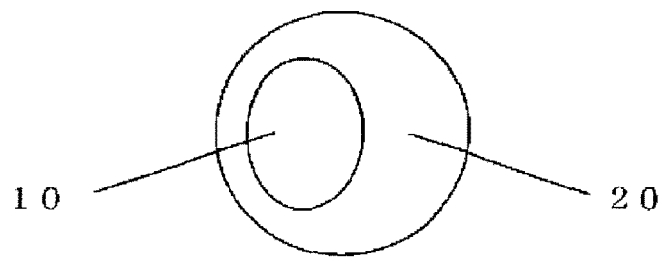

CRIMPED CONJUGATED FIBER AND NON-WOVEN FABRIC COMPRISING THE FIBER

TECHNICAL FIELD

The present invention relates to crimped conjugated fibers and a non-woven fabric comprising the fibers.

BACKGROUND ART

Polypropylene non-woven fabrics have excellent properties such as breathability and softness and are used as sanitary materials including disposable diapers and sanitary napkins. However, further improvements in their properties have been required. For example, polypropylene non-woven fabrics improved in softness, bulkiness and mechanical strength are desired.

To obtain non-woven fabrics having excellent softness and bulkiness, various methods have been proposed in which non-woven fabrics are formed of crimped polypropylene fibers. For example, Patent Document 1 discloses non-woven fabrics that comprise conjugated fibers having a crimpable cross-sectional configuration wherein the conjugated fibers comprise a first component comprising propylene polymer and a second component comprising polypropylene with different physical properties from the first component. The second polypropylene is selected from the group consisting of high MFR polypropylenes, low polydispersity polypropylenes, amorphous polypropylenes and elastic (elastomeric) polypropylenes. According to the disclosure, by melt spinning the first component and the second component having different physical properties from each other, the resultant conjugated fibers give crimped fibers capable of forming non-woven fabrics with excellent softness and elastic properties.

Patent Document 2 discloses non-woven fabrics that comprise parallel type crimped conjugated fibers comprising ethylene/propylene random copolymer and polypropylene.

In Patent Document 1, crimped conjugated fibers are obtained from a combination of polypropylenes having dissimilar properties. In detail, Example 1 discloses a combination of polypropylenes having differing MFR and molecular weight distribution in which parallel type conjugated fibers are formed from a first polypropylene having an MFR of 35 and a polydispersity number of 3 and a second polypropylene having an MFR of 25 and a polydispersity number of 2.

The conjugated fibers obtained by combining ethylene/propylene random copolymer and polypropylene that differ in crystallization rate, as described in Patent Document 2, is excellent in crimp properties. However, depending on applications, non-woven fabrics further excellent in crimp properties and bulkiness are desired.

CITATION LIST

Patent Documents

Patent Document 1: U.S. Pat. No. 6,454,989
Patent Document 2: JP-A-H07-197367

SUMMARY OF THE INVENTION

Technical Problem

It is an object of the present invention to obtain crimped conjugated fibers having further excellent crimp properties compared with conventional crimped fibers.

Technical Solution

The present inventors studied diligently and have found that more highly crimped conjugated fibers, for example conjugated fibers having an eccentric core-sheath configuration, are obtained from two kinds of propylene polymers differing in melting point by constituting the core from a propylene polymer with a high melting point having a larger Mz/Mw than that of a propylene polymer with a low melting point that constitutes the sheath. The present invention has been completed based on the finding.

An aspect of the present invention is crimped conjugated fibers having a crimpable cross-sectional configuration wherein a cross section of the fibers comprises at least two portions: a portion (a) and a portion (b), the mass ratio of the portion (a) to the portion (b) [(a):(b)] is in the range of 10:90 to 60:40, the portion (a) comprises a propylene polymer (A) and the portion (b) comprises a propylene/α-olefin random copolymer (B), the propylene polymer (A) has Mz/Mw(A) and the propylene/α-olefin random copolymer (B) has Mz/Mw(B) wherein the difference thereof [Mz/Mw(A)−Mz/Mw(B): ΔMz/Mw] is in the range of 0.10 to 2.2, and the propylene polymer (A) has a melting point [Tm(A)] and the propylene/α-olefin random copolymer (B) has a melting point [Tm(B)] wherein the difference thereof exceeds 10° C.

Advantageous Effect of the Invention

The crimped conjugated fibers of the present invention have further excellent crimp properties compared with conventional crimped conjugated fibers composed of a propylene homopolymer and a propylene/α-olefin random copolymer, and therefore a non-woven fabric excellent in bulkiness and softness can be provided.

BRIEF DESCRIPTION OF THE DRAWINGS

FIG. 1 is a perspective view showing an embodiment of a crimped conjugated fiber according to the present invention.

FIG. 2 is a view for explaining a softness test for a non-woven fabric.

FIG. 3 is a cross-sectional view of a crimped conjugated fiber according to the present invention.

FIG. 4 is a cross-sectional view of a crimped conjugated fiber according to the present invention.

FIG. 5 is a cross-sectional view of a crimped conjugated fiber according to the present invention.

FIG. 6 is a cross-sectional view of a crimped conjugated fiber according to the present invention.

FIG. 7 is a cross-sectional view of a crimped conjugated fiber according to the present invention.

FIG. 8 is a cross-sectional view of a crimped conjugated fiber according to the present invention.

DESCRIPTION OF EMBODIMENTS

<Propylene Polymer (A)>

In the crimped conjugated fibers of the present invention having a crimpable cross-sectional configuration wherein a cross section of the fibers comprises at least two portions: a portion (a) and a portion (b) (hereinafter, also referred to as the "crimped conjugated fibers"), the propylene polymer (A) for forming the portion (a) usually has a melt flow rate (MFR) (ASTM D-1238, 230° C., 2160 g load) of 20 to 100 g/10 min, preferably 30 to 80 g/10 min. If MFR of the propylene polymer is less than 20 g/10 min, the melt viscosity is high and the spinnability is poor. If MFR of the propylene polymer exceeds 100 g/10 min, an obtainable non-woven fabric may have poor tensile strength.

The propylene polymer (A) according to the present invention has a higher melting point than the melting point of the propylene/α-olefin random copolymer (B) for forming the portion (b) of the crimped conjugated fibers, wherein the difference thereof exceeds 10° C., preferably in the range of 12 to 40° C. By making the difference of the melting point larger, the conjugated fibers have further excellent crimp properties.

The propylene polymer (A) according to the present invention usually has a melting point of not lower than 155° C., preferably in the range of 157 to 165° C. In the case of a propylene polymer having a melting point of lower than 155° C., it may be difficult for the difference with the melting point of the propylene/α-olefin random copolymer (B) to exceed 10° C.

The propylene polymer (A) according to the present invention is a propylene polymer containing propylene as a main component, with examples including a propylene homopolymer and a propylene/α-olefin random copolymer of propylene and a small amount, e.g., not more than 2 mol %, preferably not more than 1 mol %, of one or more α-olefins such as ethylene, 1-butene, 1-pentene, 1-hexene, 1-octene, 1-decene, 3-methyl-1-butene, 3-methyl-1-pentene, 3-ethyl-1-pentene, 4-methyl-1-pentene and 4-methyl-1-hexene, for example a propylene/ethylene random copolymer and a propylene/ethylene/1-butene random copolymer. The propylene polymer (A) according to the present invention is preferably a propylene homopolymer.

The ratio [Mz/Mw(A)] of Z-average molecular weight (Mz) to weight average molecular weight (Mw) of the propylene polymer (A) according to the present invention is not particularly limited as long as the difference with Mz/Mw(B) of the propylene/α-olefin random copolymer (B), described later, i.e., [(Mz/Mw(A))−(Mz/Mw(B)):ΔMz/Mw] is in the range of 0.10 to 2.2. The ratio Mz/Mw(A) is usually 2.0 or more, preferably in the range of 2.1 to 4.5, more preferably 2.1 to 3.0. The propylene polymer having [Mz/Mw(A)] of more than 4.5 may have poor spinnability.

When the propylene polymer (A) has Mz/Mw(A) within the above range, it is easy to make a combination of the propylene polymer (A) and the propylene/α-olefin random copolymer (B) such that the difference between Z-average molecular weight (Mz) to weight average molecular weight (Mw) ratio [Mz/Mw(A)] of the propylene polymer (A), and Z-average molecular weight (Mz) to weight average molecular weight (Mw) ratio [Mz/Mw(B)] of the propylene/α-olefin random copolymer (B), i.e., [(Mz/Mw(A))−(Mz/Mw(B)):Δ(Mz/Mw)], is in the range of 0.10 to 2.2.

The propylene polymer (A) according to the present invention usually has Mw in the range of 150,000 to 250,000, and Mz in the range of 300,000 to 600,000.

The propylene polymer (A) according to the present invention usually has a ratio of weight average molecular weight (Mw) to number average molecular weight (Mn), i.e., molecular weight distribution [Mw/Mn (A)], in the range of 2.0 to 4.0, preferably 2.2 to 3.5.

In the present invention, Mz, Mw, Mn, Mz/Mw(A) and Mw/Mn (A) of the propylene polymer (A) may be determined by GPC (gel permeation chromatography) as will be described later.

The propylene polymer (A) according to the present invention may be obtained by homopolymerizing propylene or copolymerizing propylene and a small amount of α-olefin by slurry polymerization, gas-phase polymerization or bulk polymerization using a Ziegler-Natta catalyst that contains a titanium-containing solid transition metal component and an organometallic component or a metallocene catalyst that contains a transition metal compound of Group IV to VI of periodic table with at least one cyclopentadienyl skeleton and a cocatalyst component. At this time, propylene polymers differing in MFR, in particular a propylene polymer having an MFR and a small amount of a propylene polymer having an MFR lower than the other propylene polymer may be mixed together or produced by multistage polymerization so that Mz, Mw and Mz/Mw will be in the above-described ranges; alternatively, a propylene polymer having the above Mz, Mw and Mz/Mw may be produced directly.

The Mw/Mn(A) and Mz/Mw(A) of the propylene polymer (A) may be controlled by using specific catalysts and adjusting the polymerization conditions, or by decomposing the polymer with peroxides or the like, or by mixing two or more kinds of polymers differing in molecular weight.

As the propylene polymer (A) according to the present invention, a commercially available propylene polymer may be used, with examples including NOVATEC PP SA06A manufactured and sold by Japan Polypropylene Corporation.

The propylene polymer (A) according to the present invention may be blended with known additives or other polymers as required while still achieving the objects of the present invention. Exemplary additives are antioxidants, weathering stabilizers, light stabilizers, antistatic agents, anti-fogging agents, anti-blocking agents, lubricants, nucleating agents and pigments.

<Propylene/α-Olefin Random Copolymer (B)>

The propylene/α-olefin random copolymer (B) for forming the portion (b) of the crimped conjugated fibers of the present invention usually has a melt flow rate (MFR) (ASTM D-1238, 230° C., 2160 g load) of 20 to 100 g/10 min, preferably 30 to 80 g/10 min. If MFR of the propylene polymer is less than 20 g/10 min, the melt viscosity is high and the spinnability is poor. If MFR of the propylene polymer exceeds 100 g/10 min, an obtainable non-woven fabric may have poor tensile strength.

The propylene/α-olefin random copolymer (B) according to the present invention has a lower melting point than the melting point of the propylene polymer (A) for forming the portion (a) of the crimped conjugated fibers of the present invention, wherein the difference thereof exceeds 10° C., preferably in the range of 12 to 40° C.

The propylene/α-olefin random copolymer (B) according to the present invention usually has a melting point in the range of 120 to 155° C., preferably 125 to 150° C. The copolymer having a melting point of lower than 120° C. may have poor heat resistance. On the other hand, in the case of the propylene polymer having a melting point of higher than 155° C., it may be difficult for the difference with the melting point of the propylene polymer (A) to exceed 10° C.

The propylene/α-olefin random copolymer (B) according to the present invention is a random copolymer of propylene with an α-olefin, specifically, one or more α-olefins (excluding propylene) such as ethylene, 1-butene, 1-pentene, 1-hexene, 1-octene, 1-decene, 3-methyl-1-butene, 3-methyl-1-pentene, 3-ethyl-1-pentene, 4-methyl-1-pentene and 4-methyl-1-hexene, the copolymer having a melting point falling within the above range and usually containing the α-olefin in an amount of 2 to 10 mol %.

The propylene/α-olefin random copolymer (B) according to the present invention preferably has a ratio [Mz/Mw(B)] of Z-average molecular weight (Mz) to weight average molecular weight (Mw) of not more than 2.5, more preferably not more than 2.3.

The propylene/α-olefin random copolymer (B) according to the present invention usually has Mw in the range of 150,000 to 250,000, and Mz in the range of 300,000 to 600,000.

The propylene/α-olefin random copolymer (B) according to the present invention usually has a ratio of weight average molecular weight (Mw) to number average molecular weight (Mn), i.e., molecular weight distribution [Mw/Mn (B)], in the range of 2.0 to 4.0, and preferably 2.2 to 3.5.

In the present invention, Mz, Mw, Mn, Mz/Mw(B) and Mw/Mn(B) of the propylene/α-olefin random copolymer (B) may be determined by GPC (gel permeation chromatography) as will be described later.

The propylene/α-olefin random copolymer (B) according to the present invention may be produced in a polymerization process similar to that for the propylene polymer (A). At this time, a propylene/α-olefin random copolymer having an MFR and a small amount of a propylene/α-olefin random copolymer having an MFR differing from the other propylene/α-olefin random copolymer may be mixed together or produced by multistage polymerization so that Mz, Mw and Mz/Mw will be in the above-described ranges; alternatively, a propylene/α-olefin random copolymer having the above Mz, Mw and Mz/Mw may be produced directly.

The Mw/Mn(B) and Mz/Mw(B) of the propylene/α-olefin random copolymer (B) may be controlled by using specific catalysts and adjusting the polymerization conditions, or by decomposing the polymer with peroxides or the like, or by mixing two or more kinds of polymers differing in molecular weight.

As the propylene/α-olefin random copolymer (B) according to the present invention, a commercially available propylene polymer may be used, with examples including Prime Polypro S119 manufactured and sold by Prime Polymer Co., Ltd.

The propylene/α-olefin random copolymer (B) according to the present invention may be blended with known additives or other polymers as required while still achieving the objects of the present invention. Exemplary additives are antioxidants, weathering stabilizers, light stabilizers, anti-static agents, anti-fogging agents, anti-blocking agents, lubricants, nucleating agents and pigments.

<Crimped Conjugated Fibers>

The crimped conjugated fibers of the present invention comprise the propylene polymer (A) and the propylene/α-olefin random copolymer (B) and have a crimpable cross-sectional configuration wherein a cross section of the fibers comprises at least two portions: a portion (a) and a portion (b), the mass ratio of the portion (a) to the portion (b) [(a):(b)] is in the range of 10:90 to 60:40, the portion (a) comprises the propylene polymer (A) and the portion (b) comprises the propylene/α-olefin random copolymer (B), the difference between Mz/Mw(A) of the propylene polymer (A) and Mz/Mw(B) of the propylene/α-olefin random copolymer (B), [Mz/Mw(A)−Mz/Mw(B):ΔMz/Mw], is in the range of 0.10 to 2.2, and the difference between the melting point [Tm(A)] of the propylene polymer (A) and the melting point [Tm(B)] of the propylene/α-olefin random copolymer (B), [ΔTm=Tm (A)−Tm(B)], exceeds 10° C.

In an embodiment, the crimpable cross-sectional configuration may be an eccentric core-sheath configuration in which the core is the portion (a) formed of the propylene polymer (A) with larger Mz/Mw, and the sheath is the portion (b) formed of the propylene/α-olefin random copolymer (B) with smaller Mz/Mw. The core (the portion (a)) may be completely covered with the sheath of the propylene/α-olefin random copolymer (B) with smaller Mz/Mw, or part of the core may be exposed on the surface of the crimped conjugated fibers. The joint between the core and the sheath may be straight or curved.

In an embodiment, the joint between the core and the sheath may be straight and part of the core may be exposed on the surface of the crimped conjugated fibers, a configuration known as a side-by-side configuration.

<Mass Ratio of the Portion (a) to the Portion (B)>

In the crimped conjugated fibers of the present invention, the mass ratio of the portion (a) to the portion (b) [(a):(b)] is in the range of 10:90 to 60:40, preferably 10:90 to 50:50, more preferably 20:80 to 40:60. If the mass ratio of the portion (a) to the portion (b) is in excess of or below the above range, crimp properties are deteriorated.

<ΔMz/Mw>

The difference between Mz/Mw (A) of the propylene polymer (A) for forming the portion (a) and Mz/Mw(B) of the propylene/α-olefin random copolymer (B) for forming the portion (b), [Mz/Mw(A)−Mz/Mw(B):ΔMz/Mw], is in the range of 0.10 to 2.2, preferably 0.20 to 2.2, more preferably 0.25 to 2.0. If a propylene polymer and a propylene/α-olefin random copolymer are used wherein ΔMz/Mw is less than 0.10, crimp properties may be deteriorated. If a propylene polymer and a propylene/α-olefin random copolymer are used wherein ΔMz/Mw exceeds 2.2, the spinnability may be deteriorated. Herein, Mz is known as Z-average molecular weight and is defined by Equation (1) below:

$$Mz = \frac{\sum M_i^3 N_i}{\sum M_i^2 N_i} \quad (1)$$

In Equation (1), $M_i$ is the molecular weight of the polymer (the propylene polymer (A) and the propylene/α-olefin random copolymer polymer (B); hereinafter, referred to as the "propylene polymer" when these two polymers are combined) and $N_i$ is the number of moles of the polymer (propylene polymer).

In general, Mz is considered to reflect more precisely high-molecular weight components in a polymer. Therefore, the Mz/Mw indicates a molecular weight distribution reflecting more precisely high-molecular weight components than the usual molecular weight distribution Mw/Mn. The molecular weight distribution Mz/Mw affects fiber crimp properties.

<ΔMw/Mn>

As long as ΔMz/Mw is in the range described above, an absolute value of the difference between Mw/Mn(A) of the propylene polymer (A) and Mw/Mn(B) of the propylene/α-olefin random copolymer (B) [Mw/Mn(A)−Mw/Mn(B): ΔMw/Mn] may be 1.5 or below, in which case obtainable conjugated fibers still have excellent crimps properties. Even when an absolute value of ΔMw/Mn is in the range of 0.3 to 1.0, crimps are developed. The ratio Mw/Mn is usually known as the molecular weight distribution (polydispersity degree) indicating the degree of molecular weight distribution of a polymer. If ΔMw/Mn is excessively large, flow properties and crystallization behaviors greatly differ between one material (the portion (a)) and another material (the portion (b)), possibly resulting in deteriorated fiber spinnability. In the present invention, the numerical ranges indicated with "to" include the numbers at the sides of the "to".

ΔMz/Mw and ΔMw/Mn are obtained by determining, by GPC analysis, the ratios Mz/Mw and the ratios Mw/Mn each for the propylene polymer (A) and the propylene/α-olefin random copolymer (B) that form the portion (a) and the portion (b) respectively, and calculating an absolute value of the difference thereof.

In the present invention, GPC analysis is performed under the following conditions.

(1) 30 mg of the propylene polymer is completely dissolved in 20 mL of o-dichlorobenzene at 145° C.

(2) The solution is filtered through a sintered filter having a pore size of 1.0 μm to provide a sample.

(3) The sample is analyzed by GPC and the average molecular weight and molecular weight distribution curve are obtained with reference to polystyrene (PS) standard.

The measurement apparatus and conditions are as follows.

Measurement apparatus: Gel permeation chromatograph Alliance GPC 2000 (manufactured by Waters)

Analyzer: Data processing software Empower 2 (manufactured by Waters)

Columns: Two TSK gel GMH6-HT columns+two TSK gel GMH6-HTL columns (each 7.5 mm in inner diameter× 30 cm, manufactured by TOSOH CORPORATION)

Column temperature: 140° C.

Mobile phase: o-dichlorobenzene (containing 0.025% of butylated hydroxytoluene (BHT))

Detector: Differential refractometer

Flow rate: 1 mL/min

Sample concentration: 30 mg/20 mL

Injection amount: 500 μL

Sampling time intervals: 1 sec

Column calibration: Monodisperse polystyrenes (manufactured by TOSOH CORPORATION)

Molecular weight conversion: PS conversion/standard conversion methods

<ΔTm>

The difference between the melting point of the propylene polymer (A) for forming the portion (a) of the present invention and the melting point of the propylene/α-olefin random copolymer (B) for forming the portion (b) of the present invention exceeds 10° C. The difference is preferably in the range of 12 to 40° C.

The value of ΔTm is obtained by determining the melting points of the propylene polymer (A) and the propylene/α-olefin random copolymer (B) that are raw materials for the portion (a) and the portion (b) respectively and calculating an absolute value of the difference thereof.

In the present invention, the melting point is measured as follows.

(1) The propylene polymer is set in a pan of a differential scanning calorimeter (DSC) manufactured by PerkinElmer Co., Ltd. The pan is heated from 30 to 200° C. at a rate of 10° C./min, held at 200° C. for 10 minutes, and cooled to 30° C. at a rate of 10° C./min.

(2) The pan is heated again from 30 to 200° C. at a rate of 10° C./min, and the melting point is obtained from the peak recorded during this second heating process.

<MFR Ratio>

The ratio of the MFR of the propylene polymer (A) for forming the portion (a) of the present invention to the MFR of the propylene/α-olefin random copolymer (B) for forming the portion (b) of the present invention (hereinafter, also the MFR ratio), which is not particularly limited, is usually in the range of 0.8 to 1.2. In the present invention, conjugated fibers having excellent crimp properties are obtained even when the MFR ratio is within the above range. The MFR of the propylene polymer (A) and the propylene/α-olefin random copolymer (B) according to the present invention are preferably in the range of 20 to 100 g/10 min.

In the present invention, MFR is determined at 230° C. under 2160 g load in accordance with ASTM D 1238.

<Crimp Number and Other Properties of Crimped Conjugated Fiber>

The number of crimps of the crimped conjugated fibers of the present invention is determined in accordance with JIS L 1015. The number of crimps is usually 19 or more, preferably 20 to 50, per 25 mm of the fiber. If the number of crimps is less than the lower limit, the crimped fibers may not achieve characteristics such as bulkiness by the three dimensional helical structure. If the number of crimps is larger than the upper limit, uniform distribution of the fibers is difficult and an obtainable non-woven fabric may have deteriorated texture or mechanical strength.

The diameter of the crimped conjugated fibers of the present invention is not particularly limited, but is usually in the range of 0.5 to 5 denier, preferably 0.5 to 3 denier. This fineness ensures excellent spinnability and crimp properties, and mechanical strength of an obtainable non-woven fabric.

FIG. 1 is a perspective view showing an embodiment of the crimped conjugated fibers according to the present invention. In the figure, 10 indicates the portion (a) and 20 indicates the portion (b).

The crimped conjugated fibers of the present invention have a crimpable cross-sectional configuration wherein a cross section of the fibers comprises at least two portions: the portion (a) and the portion (b). In the cross section of the crimped conjugated fibers, the proportions of the portion (a) and the portion (b) are such that the mass ratio [(a):(b)] is in the range of 10:90 to 60:40, preferably 10:90 to 50:50, more preferably 20:80 to 40:60.

The crimped conjugated fibers may have any shapes without limitation as long as they have a crimpable cross-sectional configuration. Exemplary shapes include side-by-side (parallel) crimped conjugated fibers in which the portion (a) and the portion (b) are arranged adjacent to each other, and core-sheath crimped conjugated fibers in which the portion (a) forms a core (a') and the portion (b) forms a sheath (b').

FIGS. 3 to 8 show other cross-sectional views of crimped conjugated fibers according to the present invention. In the figures, 10 indicates the portion (a) and 20 indicates the portion (b).

The term "core-sheath crimped conjugated fibers" refers to fibers which have a core and a sheath and are crimped. The core (a') is arranged with at least part thereof being surrounded by a polymer different from the core (a') in the fiber cross section and extends along the length of the fiber. The sheath (b') is arranged so as to surround at least part of the core (a') in the fiber cross section and extends along the length of the fiber. In an eccentric core-sheath crimped conjugated fiber, the core (a') and the sheath (b') are located non-concentrically in the cross section of the fiber. The eccentric core-sheath crimped conjugated fibers include an exposed type in which the side of the core (a') is exposed, and a non-exposed type in which the core (a') is fully occluded. In the present invention, eccentric core-sheath crimped conjugated fibers of the exposed type are preferred because they show excellent crimp properties. The cross sectional joint between the core (a') and the sheath (b') may be straight or curved. The core may be circular, elliptical or square in cross section.

The crimped conjugated fibers of the present invention may be staple fibers or continuous fibers. Continuous fibers are preferable because an obtainable non-woven fabric does not have loss of the crimped conjugated fibers and excellent fuzzing resistance is achieved.

<Non-Woven Fabric>

The non-woven fabric of the present invention is made of the above crimped conjugated fibers. The non-woven fabric usually has a basis weight (mass per unit area of the non-woven fabric) of 3 to 100 g/m$^2$, preferably 7 to 60 g/m$^2$.

The non-woven fabric of the present invention preferably comprises the crimped conjugated fibers that are continuous fibers. In view of productivity, the non-woven fabric is particularly preferably spunbonded non-woven fabric of such fibers.

In the non-woven fabric of the present invention, it is preferable that the crimped conjugated fibers are thermally fusion bonded by embossing, whereby the fibers maintain stability and strength.

<Non-Woven Fabric Laminate>

The non-woven fabric comprising the crimped conjugated fibers of the present invention (hereinafter, also referred to as the crimped conjugated fiber non-woven fabric to be distinguished from a usual non-woven fabric) may be laminated with various layers depending on use.

In detail, the crimped conjugated fiber non-woven fabric may be laminated with knitted fabrics, woven fabrics, non-woven fabrics, films and the like. The crimped conjugated fiber non-woven fabric may be laminated (joined) with such other layers by known methods including thermal fusion bonding methods such as heat embossing and ultrasonic fusion bonding, mechanical entanglement methods such as needle punching and water jetting, adhesive bonding methods with hot melt adhesives or urethane adhesives, and extrusion laminating methods.

The non-woven fabrics laminated with the crimped conjugated fiber non-woven fabric include various known non-woven fabrics such as spunbonded non-woven fabrics, meltblown non-woven fabrics, wet non-woven fabrics, dry non-woven fabrics, dry pulp non-woven fabrics, flash-spun non-woven fabrics and spread-fiber non-woven fabrics.

The materials for such non-woven fabrics may be conventional thermoplastic resins. Examples thereof include homopolymers and copolymers of α-olefins such as ethylene, propylene, 1-butene, 1-hexene, 4-methyl-1-pentene and 1-octene, namely, polyolefins such as high-pressure low-density polyethylenes, linear low-density polyethylenes (LLDPE), high-density polyethylenes, polypropylenes, polypropylene random copolymers, poly-1-butene, poly-4-methyl-1-pentene, ethylene/propylene random copolymers, ethylene/1-butene random copolymers and propylene/1-butene random copolymers; polyesters such as polyethylene terephthalate, polybutylene terephthalate and polyethylene naphthalate; polyamides such as nylon-6, nylon-66 and polymethaxyleneadipamide; polyvinyl chloride, polyimides, ethylene/vinyl acetate copolymers, polyacrylonitriles, polycarbonates, polystyrenes, ionomers and thermoplastic polyurethanes; and mixtures of these resins. Of these, high-pressure low-density polyethylenes, linear low-density polyethylenes (LLDPE), high-density polyethylenes, polypropylenes, polypropylene random copolymers, polyethylene terephthalate and polyamides are preferred.

In a preferred embodiment of the present invention, the crimped conjugated fiber non-woven fabric is laminated with a spunbonded non-woven fabric made of an ultrafine fiber (fineness: 0.8 to 2.5 denier, more preferably 0.8 to 1.5 denier) and/or a meltblown non-woven fabric. Specific examples include:

two-layer laminates such as spunbonded non-woven fabric (ultrafine fiber)/crimped conjugated fiber non-woven fabric, and meltblown non-woven fabric/crimped conjugated fiber non-woven fabric;

three-layer laminates such as spunbonded non-woven fabric (ultrafine fiber)/crimped conjugated fiber non-woven fabric/spunbonded non-woven fabric (ultrafine fiber), spunbonded non-woven fabric (ultrafine fiber)/crimped conjugated fiber non-woven fabric/meltblown non-woven fabric, and spunbonded non-woven fabric (ultrafine fiber)/meltblown non-woven fabric/crimped conjugated fiber non-woven fabric; and laminates having four or more layers such as spunbonded non-woven fabric (ultrafine fiber)/crimped conjugated fiber non-woven fabric/meltblown non-woven fabric/spunbonded non-woven fabric (ultrafine fiber), and spunbonded non-woven fabric (ultrafine fiber)/crimped conjugated fiber non-woven fabric/meltblown non-woven fabric/crimped conjugated fiber non-woven fabric/spunbonded non-woven fabric (ultrafine fiber).

The basis weight of each non-woven fabric layer in the laminate is preferably in the range of 2 to 25 g/m$^2$. The spunbonded non-woven fabric made of the ultrafine fibers described above may be obtained by controlling (selecting) spunbonding conditions. The non-woven fabric laminates benefit from the bulkiness and softness of the crimped conjugated fiber non-woven fabric of the present invention and also achieve excellent surface smoothness and improved water resistance.

The films laminated with the crimped conjugated fiber non-woven fabric of the present invention are preferably breathable (moisture permeable) films in order to take advantage of the breathability of the crimped conjugated fiber non-woven fabric. Various known breathable films may be used, with examples including films of moisture permeable thermoplastic elastomers such as polyurethane elastomers, polyester elastomers and polyamide elastomers; and porous films obtained by stretching thermoplastic resin films containing inorganic or organic fine particles to create pores in the films. Preferred thermoplastic resins for the porous films are high-pressure low-density polyethylenes, linear low-density polyethylenes (LLDPE), high-density polyethylenes, polypropylenes, polypropylene random copolymers and compositions containing these polyolefins.

The laminates with the breathable films are cloth-like composite materials having bulkiness and softness of the crimped conjugated fiber non-woven fabric of the present invention and very high water resistance.

<Process for Producing Non-Woven Fabric>

The non-woven fabric of the present invention may be produced by any known process while still achieving the advantageous effects of the present invention. A preferred production process is described below.

The non-woven fabric of the present invention is preferably produced through:

(1) a step in which the propylene polymer (A) and the propylene/α-olefin random copolymer (B) that are raw materials for the portion (a) and the portion (b) respectively are separately molten in at least two extruders and are spun from a composite spinning nozzle into conjugated fibers;

(2) a step in which the conjugated fibers are quenched, then drawn and attenuated to develop crimps, and the crimped conjugated fibers are deposited on a collecting belt to a desired thickness; and (3) a step in which the deposited conjugated fibers are entangled.

This process is called a spunbonding process.

Step (1)

In this step, known extruders and composite spinning nozzles may be used. The melting temperature is not particularly limited but is preferably higher by approximately 50° C. than the melting point of the propylene polymer. The spinnability in this step is evaluated based on the presence or absence of fiber breakage within a predetermined time.

Step (2)

In this step, the molten fibers are preferably quenched by blowing air. The air temperature may be 10 to 40° C. The quenched fibers may be controlled to a desired diameter by the tensile force of blowing air. The quenched fibers develop crimps. The collecting belt may be conventional but is preferably one that is capable of conveying the crimped fibers, for example a belt conveyer.

Step (3)

The entanglement treatment in this step may be performed for example by applying water jet or ultrasonic wave to the deposited crimped conjugated fibers (hereinafter, also referred to simply as "fibers") or by thermally fusion bonding the fibers by embossing or hot air.

In the present invention, it is particularly preferable that the crimped conjugated fibers are embossed, whereby a non-woven fabric having excellent strength is obtained. The embossing is carried out under conditions such that the embossed area percentage is 5 to 30%. The embossed area percentage represents the total area of emboss relative to the total area of the non-woven fabric. Reducing the embossed area provides a non-woven fabric with excellent softness. Increasing the embossed area gives a non-woven fabric having excellent rigidity and mechanical strength.

The embossing temperature is preferably controlled depending on the melting points of the portions (a) and (b). For the propylene polymer, the embossing temperature is usually in the range of 100 to 150° C.

EXAMPLES

The present invention will be described in greater detail by examples hereinbelow without limiting the scope of the invention.

The propylene polymers used in Examples and Comparative Examples of the present invention are listed below.
(1) Propylene Polymer (A) [Propylene Homopolymer]
(1-1) NOVATEC PP SA06A manufactured by Japan Polypropylene Corporation.
(1-2) Prime Polypro S119 manufactured by Prime Polymer Co., Ltd.
(1-3) Prime Polypro HS135 manufactured by Prime Polymer Co., LLd.
(2) Propylene/α-Olefin Random Copolymer (B) [Propylene/ Ethylene Random Copolymer]
(2-1) Prime Polypro S229R manufactured by Prime Polymer Co., Ltd.; melting point: 143° C., ethylene content: 3.0 wt % (4.5 mol %)
(2-2) A prototype manufactured by Prime Polymer Co., Ltd. (copolymer obtained by thermally degrading a propylene/ ethylene random copolymer having an MFR of 7 with a peroxide in order for the copolymer to have an MFR of 60); melting point: 146° C., ethylene content: 2.3 wt % (3.3 mol %) (Sample 8)
(2-3) A prototype manufactured by Prime Polymer Co., Ltd. (copolymer obtained by thermally degrading a propylene/ ethylene random copolymer having an MFR of 7 with a peroxide in order for the copolymer to have an MFR of 61); melting point: 143° C., ethylene content: 2.8 wt % (4.1 mol %) (Sample 9)
(2-4) A prototype manufactured by Prime Polymer Co., Ltd. (copolymer obtained by thermally degrading a propylene/ ethylene random copolymer having an MFR of 7 with a peroxide in order for the copolymer to have an MFR of 55); melting point: 140° C., ethylene content: 3.2 wt % (4.6 mol %) (Sample 10)
(2-5) A prototype manufactured by Prime Polymer Co., Ltd. (copolymer obtained by thermally degrading a propylene/ ethylene random copolymer having an MFR of 3.5 polymerized by using a metallocene catalyst, with a peroxide in order for the copolymer to have an MFR of 40); melting point: 128° C., ethylene content: 3.6 wt % (5.3 mol %) (Sample 11)

Example 1

A propylene polymer (A) for forming a core was SA06A. A propylene/α-olefin random copolymer (B) for forming a sheath was S229R. The polymers were melt-spun by spunbonding method.

Single-screw extruders were used and the propylene polymer (A) and the propylene/α-olefin random copolymer (B) were molten at 200° C.

The polymers were spun into continuous fibers in which the mass ratio of a core h1 to a sheath h2 was 20:80. The fineness was 2.3 denier.

The resultant eccentric core-sheath crimped conjugated continuous fibers that were melt-spun were deposited on a collecting surface to form a non-woven fabric. The non-woven fabric was embossed at 125° C. The embossed area percentage was 18%. The embossed non-woven fabric had a basis weight of 25 g/m². The resultant crimped conjugated continuous fibers and non-woven fabric were evaluated for properties by the following methods.

(1) Number of Crimps The number of crimps was measured in accordance with JIS L 1015.

The crimp properties were evaluated AA when the number of crimps was 20 or more per 25 mm, BB when the number of crimps was from 5 to less than 20 per 25 mm, and CC when the number of crimps was from 0 to less than 5 per 25 mm.

(2) 2% Tensile Elongation Strength

A test piece 600 mm in MD×100 mm in CD was prepared.

The test piece was wound around an iron rod 10 mm in diameter and 700 mm in length and was formed into a tubular sample having a length of 600 mm. The sample was tensile tested with a chuck distance of 500 mm at a tension rate of 500 mm/min, and the load at 1.5% elongation and at 2.5% elongation was measured. The 2% tensile elongation strength was obtained from the following equation:

2% tensile elongation strength (N/cm)=(load at 2.5% elongation−load at 1.5% elongation)/10 cm×100

A non-woven fabric having a higher value of 2% tensile elongation strength were evaluated to have higher rigidity, and a non-woven fabric having a lower value were evaluated to have higher softness.

(3) Softness

The softness was evaluated by a cantilever method in accordance with JIS L 1096. In detail, the evaluation was made as follows.
1) A 2×15 cm test piece 30 was prepared and was placed on a test table 40 as illustrated in FIG. 2.
2) The test piece 30 was slowly pushed in the direction of arrow until it bent, and a distance 50 was measured.
3) The above testing was carried out along each of MD and CD of the test pieces.

A non-woven fabric having a higher value of this testing was evaluated to have higher rigidity, and a non-woven fabric having a lower value was evaluated to have higher softness.

(4) Thickness

Five test pieces (100 mm×100 mm) were sampled from a test sample. With respect to each test piece, the thickness was measured at arbitrary three points with a constant pressure thickness gauge (manufactured by OZAKI MFG. CO. LTD.). The gauge head had a diameter of 16 mm, and the load was 3.6 g/cm$^2$. The value was read after 30±5 seconds after the gauge head completely contacted the test piece. The results of the five test pieces were averaged to determine the thickness. A non-woven fabric having a higher value of thickness was evaluated to have higher bulkiness.

The measurement results are set forth in Table 2.

Example 2

Crimped conjugated continuous fibers and a non-woven fabric were obtained in the same manner as in Example 1, except that the propylene polymer (A) used in Example 1 was changed to a composition (blend) of propylene homopolymers S119/HS135=96/4 (mass ratio). The measurement results for the crimped conjugated continuous fibers and the non-woven fabric are set forth in Table 1.

Example 3

Crimped conjugated continuous fibers and a non-woven fabric were obtained in the same manner as in Example 2, except that the mass ratio of the propylene polymer (A) to the propylene/α-olefin random copolymer (B) used in Example 2 was 50:50. The measurement results for the crimped conjugated continuous fibers and the non-woven fabric are set forth in Table 1.

Example 4

Crimped conjugated continuous fibers and a non-woven fabric were obtained in the same manner as in Example 1, except that using the propylene polymer (A) and the propylene/α-olefin random copolymer (B) that were polymers as indicated in Table 1, the mass ratio of a core h3 to a sheath h4 in the continuous fibers was 30:70. The measurement results for the crimped conjugated continuous fibers and the non-woven fabric are set forth in Table 1.

Example 5

Crimped conjugated continuous fibers were obtained in such a manner that the propylene polymer (A) was S119, the propylene/α-olefin random copolymer (B) was a polymer as indicated in Table 1, and the mass ratio of a core h3 to a sheath h4 in the continuous fibers was 20:80. The measurement results for the crimped conjugated continuous fibers are set forth in Table 1.

Comparative Example 1

Conjugated continuous fibers and a non-woven fabric were obtained in the same manner as in Example 1, except that the propylene polymer (A) used for the core in Example 1 was changed to S119 and this was used for the core. The measurement results for the conjugated continuous fibers and the non-woven fabric are set forth in Table 1.

Comparative Example 2

Conjugated continuous fibers and a non-woven fabric were obtained in the same manner as in Example 3, except that the propylene polymer (A) and the propylene/α-olefin random copolymer (B) used for the core and the sheath in Example 3 were both changed to S229R and this was used for the core and the sheath, and the embossing temperature was changed to 120° C. The conjugated continuous fibers did not develop crimps. The measurement results for the conjugated continuous fibers and the non-woven fabric are set forth in Table 1.

Comparative Example 3

Conjugated continuous fibers were obtained in the same manner as in Example 3, except that the propylene/α-olefin random copolymer (B) used for the sheath in Example 5 was changed to Sample 8 and this was used for the sheath. The conjugated continuous fibers did not develop crimps. The measurement results for the conjugated continuous fibers are set forth in Table 1.

Comparative Example 4

Conjugated continuous fibers were obtained in the same manner as in Example 3, except that the propylene/α-olefin random copolymer (B) used for the sheath in Example 5 was changed to Sample 9 and this was used for the sheath. The conjugated continuous fibers did not develop crimps. The measurement results for the conjugated continuous fibers are set forth in Table 1.

Comparative Example 5

Conjugated continuous fibers and a non-woven fabric were obtained in the same manner as in Example 3, except that the propylene/α-olefin random copolymer (B) used for the sheath in Example 5 was changed to Sample 10 and this was used for the sheath, and the embossing temperature was changed to 122° C. The conjugated continuous fibers did not develop crimps. The measurement results for the conjugated continuous fibers are set forth in Table 1.

TABLE 1

|  |  |  | Ex. 1 | Ex. 2 | Ex. 3 | Ex. 4 | Ex. 5 |
|---|---|---|---|---|---|---|---|
| Core | Propylene polymer (A): type of polymers |  | SA06A | S119/HS135 = 96/4 | S119/HS135 = 96/4 | SA06A | S119 |
|  | MFR | g/10 min | 59 | 58 | 58 | 59 | 63 |
|  | Mw/Mn | — | — | 3.01 | 3.30 | 3.30 | 3.01 | 3.28 |
|  | Mz/Mw | — | — | 2.53 | 2.49 | 2.49 | 2.53 | 2.24 |
|  | Melting point | ° C. | 161 | 158 | 158 | 161 | 158 |

TABLE 1-continued

| | | | | | | | |
|---|---|---|---|---|---|---|---|
| Sheath | Propylene/α-olefin random polymer (B): type of polymers | | S229R | S229R | S229R | S229R | Sample 11 |
| | MFR | g/10 min | 63 | 63 | 63 | 63 | 40 |
| | Mw/Mn | — | 2.73 | 2.73 | 2.73 | 2.73 | 2.12 |
| | Mz/Mw | — | 2.19 | 2.19 | 2.19 | 2.19 | 1.86 |
| | Melting point | °C. | 143 | 143 | 143 | 143 | 128 |
| Core:sheath ratio | | | 20:80 | 20:80 | 50:50 | 30:70 | 20:80 |
| ΔMz/Mw | | — | 0.35 | 0.30 | 0.30 | 0.35 | 0.38 |
| ΔMw/Mn | | — | 0.27 | 0.27 | 0.27 | 0.27 | 1.16 |
| MFR ratio | | — | 0.94 | 0.92 | 0.92 | 0.94 | 1.58 |
| ΔTm | | °C. | 18 | 15 | 15 | 18 | 30 |
| Melting temperature | | °C. | 200 | 200 | 200 | 200 | 200 |
| Embossing conditions | Embossed area percentage | % | 18 | 18 | 18 | 18 | — |
| | Linear pressure | N/mm | 60 | 60 | 60 | 60 | — |
| | Emboss roll temperature | °C. | 125 | 125 | 125 | 125 | — |
| | Crown roll temperature | °C. | 125 | 125 | 125 | 125 | — |
| Properties | Basis weight | g/m² | 24.7 | 24.6 | 24.8 | 25.1 | — |
| | Thickness | μm | 310 | 300 | 290 | 320 | — |
| | Porosity | % | 91.2 | 91.0 | 90.6 | 91.4 | — |
| | 2% tensile elongation strength (MD) | N/cm | 43 | 48 | 52 | 38 | — |
| | Softness in MD (distance) | mm | 43 | 44 | 48 | 42 | — |
| Crimp properties | | | AA | AA | AA | AA | AA |
| Number of crimps | | crimps/25 mm | 28.0 | 27.0 | 25.0 | 30.0 | 28.0 |
| Spinnability | | | Sufficient | Sufficient | Sufficient | Sufficient | Sufficient |

| | | | Comp. Ex. 1 | Comp. Ex. 2 | Comp. Ex. 3 | Comp. Ex. 4 | Comp. Ex. 5 |
|---|---|---|---|---|---|---|---|
| Core | Propylene polymer (A): type of polymers | | S119 | S229R | S119 | S119 | S119 |
| | MFR | g/10 min | 63 | 63 | 63 | 63 | 63 |
| | Mw/Mn | — | 3.28 | 2.73 | 3.28 | 3.28 | 3.28 |
| | Mz/Mw | — | 2.24 | 2.19 | 2.24 | 2.24 | 2.24 |
| | Melting point | °C. | 158 | 143 | 158 | 158 | 158 |
| Sheath | Propylene/α-olefin random polymer (B): type of polymers | | S229R | S229R | Sample 8 | Sample 9 | Sample 10 |
| | MFR | g/10 min | 63 | 63 | 59 | 61 | 55 |
| | Mw/Mn | — | 2.73 | 2.73 | 3.44 | 3.20 | 3.20 |
| | Mz/Mw | — | 2.19 | 2.19 | 2.77 | 2.65 | 2.71 |
| | Melting point | °C. | 143 | 143 | 146 | 143 | 140 |
| Core:sheath ratio | | | 20:80 | 20:80 | 20:80 | 20:80 | 20:80 |
| ΔMz/Mw | | — | 0.05 | 0.00 | −0.53 | −0.41 | −0.47 |
| ΔMw/Mn | | — | 0.55 | 0.00 | −0.16 | 0.08 | 0.08 |
| MFR ratio | | — | 1.00 | 1.00 | 1.07 | 1.03 | 1.15 |
| ΔTm | | °C. | 15 | 0 | 12 | 15 | 18 |
| Melting temperature | | °C. | 200 | 200 | 200 | 200 | 200 |
| Embossing conditions | Embossed area percentage | % | 18 | 18 | — | — | 18 |
| | Linear pressure | N/mm | 60 | 60 | — | — | 60 |
| | Emboss roll temperature | °C. | 125 | 120 | — | — | 122 |
| | Crown roll temperature | °C. | 125 | 120 | — | — | 122 |
| Properties | Basis weight | g/m² | 24.8 | 24.5 | — | — | 24.2 |
| | Thickness | μm | 282 | 252 | — | — | 291 |
| | Porosity | % | 90.3 | 89.3 | — | — | 90.9 |
| | 2% tensile elongation strength (MD) | N/cm | 66 | 64 | — | — | 82 |
| | Softness in MD (distance) | mm | 52 | 54 | — | — | 53 |
| Crimp properties | | | BB | CC | CC | CC | CC |
| Number of crimps | | crimps/25 mm | 18.0 | 0.0 | 0 | 0 | 0 |
| Spinnability | | | Sufficient | Sufficient | Sufficient | Sufficient | Sufficient |

INDUSTRIAL APPLICABILITY

The non-woven fabric according to the present invention has excellent properties such as spinnability, strength, softness and water resistance and is useful in side gathers, back sheets, top sheets and waist parts of disposable diapers or sanitary napkins.

REFERENCE SIGNS LIST

10 . . . portion (a)
20 . . . portion (b)
30 . . . test piece
40 . . . test table
50 . . . distance

The invention claimed is:
1. A crimped conjugated fiber having a cross-sectional configuration wherein a cross section of the fiber comprises at least two portions: a portion (a) and a portion (b),
   the mass ratio of the portion (a) to the portion (b) [(a):(b)] is in the range of 10:90 to 60:40,
   the portion (a) comprises a propylene polymer (A) and the portion (b) comprises a propylene/α-olefin random copolymer (B), the propylene polymer (A) has Mz/Mw(A) and the propylene/α-olefin random copolymer (B) has Mz/Mw(B) wherein the difference thereof [Mz/Mw(A)–Mz/Mw(B): ΔMz/Mw] is in the range of 0.10 to 2.2, and the propylene polymer (A) has a melting point [Tm(A)] and the propylene/α-olefin random copolymer (B) has a melting point [Tm(B)] wherein the difference thereof exceeds 10° C., wherein the crimped conjugated fiber has an eccentric core-sheath configuration in which the portion (a) is a core (a') and the portion (b) is a sheath (b'), and wherein [Tm(A)] is higher than [Tm(B)].

2. The crimped conjugated fiber according to claim 1, wherein the propylene polymer (A) is a propylene homopolymer.

3. A non-woven fabric comprising the crimped conjugated fiber described in claim 2.

4. The non-woven fabric according to claim 3, wherein the crimped conjugated fiber is thermally fusion bonded by embossing.

5. A non-woven fabric comprising the crimped conjugated fiber described in claim 1.

6. The non-woven fabric according to claim 5, wherein the crimped conjugated fiber is thermally fusion bonded by embossing.

* * * * *